United States Patent [19]
Goeke

[11] 3,958,956

[45] May 25, 1976

[54] METHANE PRODUCTION PROCESS AND ARRANGEMENT THEREFOR

[75] Inventor: Eberhard Goeke, Essen, Germany

[73] Assignee: Krupp-Koppers GmbH, Essen, Germany

[22] Filed: July 9, 1974

[21] Appl. No.: 486,928

[30] Foreign Application Priority Data

July 13, 1973 Germany............................ 2335659

[52] U.S. Cl.................................. 48/62 R; 23/260; 48/76; 48/197 R; 48/203; 48/212; 260/449 M
[51] Int. Cl.²...................... B01J 1/00; C07C 9/04; C07C 27/06
[58] Field of Search.................. 48/197 R, 89, 62 R, 48/76, 212, 203, 210; 260/449 M, ; 23/260, 262

[56] References Cited
UNITED STATES PATENTS

| | | | |
|---|---|---|---|
| 943,627 | 12/1909 | Elworthy | 260/449 M UX |
| 2,711,419 | 6/1955 | Milbourne | 48/197 R X |
| 3,062,632 | 11/1962 | Bailey | 48/203 |
| 3,351,564 | 11/1967 | Faatz, Jr. et al. | 260/449 M X |
| 3,379,505 | 4/1968 | Holmes et al. | 260/449 M X |
| 3,511,624 | 5/1970 | Humphries et al. | 48/197 R |
| 3,625,665 | 12/1971 | Thompson | 48/197 R X |

OTHER PUBLICATIONS

Bennett, Concise Chemical and Technical Dictionary, p. 763 (1947).

*Primary Examiner*—Joseph Scovronek
*Attorney, Agent, or Firm*—Michael J. Striker

[57] ABSTRACT

The gaseous product obtained by the partial oxidation of a fuel such as coal and/or oil is desulfurized and then admitted into a packed gas-liquid contact column. Here, the gas comes into contact with water so as to become at least partially saturated with water vapor. The gas is next conveyed to a reactor wherein it undergoes a methane-forming reaction under isothermal conditions, the methane-forming reaction taking place without previously subjecting the gas to a conversion reaction. The methane-forming reaction is carried out catalytically with a nickel-containing catalyst and deposition of carbon from the gas onto the catalyst is prevented by virtue of the water vapor present during the reaction. The quantity of water vapor present during the reaction is adjusted so as to lie between predetermined limits. After completion of the reaction, the gas is admitted into another packed gas-liquid column wherein it is cooled by contact with cooling water at which time residual water vapor in the gas condenses. Subsequent to the cooling operation, the gas may be scrubbed so as to remove carbon dioxide therefrom and thereby obtain a gas containing at least 80 volume percent methane. The cooling water is heated during the cooling operation and this cooling water, together with the condensed water vapor, is conveyed to the first-mentioned column where it is used for at least partially saturating the gas to be treated with water vapor. Excess water which is not used for the saturation is conveyed back to the second-mentioned column to be used as cooling water.

12 Claims, 1 Drawing Figure

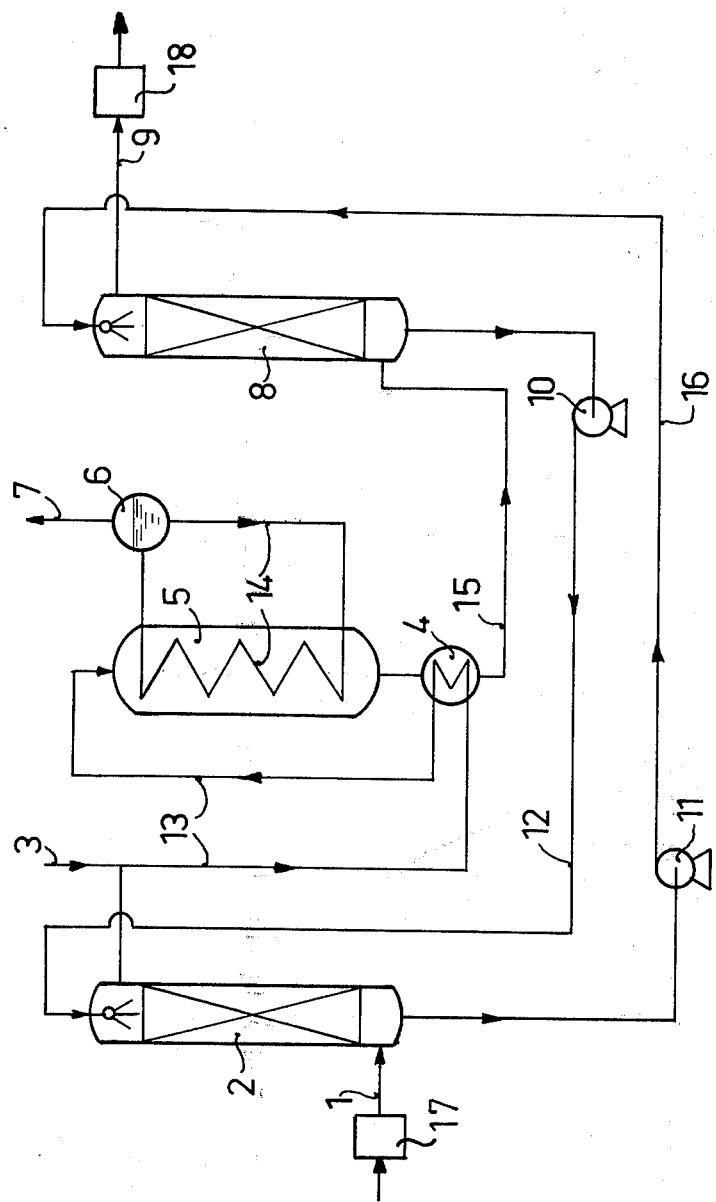

METHANE PRODUCTION PROCESS AND ARRANGEMENT THEREFOR

BACKGROUND OF THE INVENTION

The invention relates generally to the production of methane-containing gases.

Methane-containing gases of sufficiently high methane content may, for instance, be used as exchange gases for, that is, instead of, natural gas. In recent times, numerous proposals for the production of natural gas exchange gas have become known. The starting materials which may be used include coke-oven gas and liquid, lowboiling hydrocarbons such as, for example, benzine. However, it is also possible to use solid fuels such as coal or coal dust as well as high-boiling hydrocarbons such as heavy oil or heavy fuel oil.

If the latter substances, that is, fuels, are used, then it is advantageous for these starting materials to be initially subjected to a partial oxidation (gasification). This may be accomplished using known processes such as, for instance, the Koppers-Totzek process, the Shell process or the Texaco process. Which of these processes is most favorably used in a given instance depends primarily upon the type and characteristics of the starting material to be gasified. Similarly, the composition of the resulting gas of partial oxidation is dependent upon the starting material.

Normally, the gases of partial oxidation are subjected to a desulfurization subsequent to the gasification during which the sulfur compounds contained in the gases are removed therefrom in accordance with known procedures.

Since the gases resulting from partial oxidation have a high carbon monoxide content which, in any event, exceeds 45 percent by volume, it has heretofore been the practice not to immediately subject the desulfurized gas of partial oxidation to a catalytic methane-forming or methanization reaction. Thus, it has been found that an immediate reaction or transformation of the carbon monoxide-rich gas results in the deposition of carbon on the conventional nickel-containing catalyst for the methanization already within a short period of time. The reason for this is that untransformed carbon monoxide splits into a carbon component and a carbon dioxide component in the presence of these catalysts, even at lower temperatures below 200°C. Consequently, the practice until now has been to catalytically convert a portion of the carbon monoxide in the gas of partial oxidation subsequent to desulfurization. As is known, the conversion reaction proceeds according to the following relationship:

$$CO + H_2O \rightarrow H_2 + CO_2 \qquad (1)$$

The carbon dioxide formed during this reaction is then removed from the process by means of procedures which are likewise conventional.

The most diverse proven possibilities and combinations exist for the desulfurization and conversion. For example, the conversion may be carried out prior to the desulfurization since there are presently available sulfur-resistant conversion catalysts as well as sulfur-susceptible catalysts.

After the desulfurization and conversion, the gas of partial oxidation, which still has more or less of a high carbon monoxide content and which has been more or less freed of carbon dioxide, is, in accordance with the prior practice, subjected to a catalytic methanization. This methanization or methane-forming reaction proceeds predominantly in accordance with the following relationship:

$$CO + 3H_2 \rightarrow CH_4 + H_2O \qquad (2)$$

Concomitantly, methanization of carbon dioxide still remaining in the gas proceeds according to the following reaction:

$$CO_2 + 4H_2 \rightarrow CH_4 + 2H_2O \qquad (3)$$

The known procedures outlined above possess certain disadvantages, however. Thus, on the one hand, large quantities of water vapor are required for the conversion reaction since, aside from the water vapor utilized in the reaction itself, large quantities of water vapor for the equilibrium are also necessary. On the other hand, water vapor is produced during the subsequent methanization reaction and this water vapor is not put to use and must eventually be condensed out of the gas.

It has also become known, in the methanization of converted water gas, to add water vapor after the conversion to the gas which is to be transformed for the purpose of suppressing the deposition of carbon onto the methanization catalyst. Such an addition of water vapor, however, likewise gives rise to certain problems. Thus, in the first place, it is necessary to heat the water vapor to the reaction temperature for the methanization. Furthermore, the water vapor which remains untransformed must again be separated from the gas subsequent to the methanization.

SUMMARY OF THE INVENTION

It is, accordingly, a general object of the invention to provide a novel process and arrangement for the production of methane-containing gases.

An additional object of the invention is to provide a process and arrangement which enable the production of methane-containing gases to be carried out more economically than was possible heretofore.

A further object of the invention is to provide a process and arrangement which enable the production of methane-containing gases to be achieved with the introduction of lesser quantities of water vapor from external sources than was possible until now. Another object of the invention is to provide a process and arangement for the production of methanecontaining gases which enable use to be made of the water vapor generated during the methane-forming reaction.

It is also an object of the invention to provide a process and arrangement for the production of a methanecontaining gas, especially a gas having a methane content of at least 80 percent by volume, whereby the process may proceed from a gas obtained by partial oxidation (gasification) and which enable the treatment of the gas of partial oxidation to be performed more economically than heretofore and, in particular, enable the water vapor requirements to be decreased and the expenditures associated with the requisite apparatus to be reduced.

In accordance with the foregoing objects and others which will become apparent, the invention provides a process for the production of methane-containing gases wherein a gaseous substance is conveyed along a flow path and subjected to a methanization reaction in the presence of a predetermined amount of water vapor in at least one portion of the flow path. The gaseous substance is cooled with cooling water in another portion of the flow path downstream of the aforesaid one portion. Subsequent to the cooling, at least part of the cooling water is admitted into a region of the flow path such that a quantity of the cooling water is present in the aforesaid one portion of the flow path in vapor form during the reaction and at least partially constitutes the aforesaid predetermined amount of water vapor. Residual cooling water is conveyed from the aforesaid region of the flow path to the aforesaid other portion of the flow path for use in the cooling.

Thus, in one of its aspects the invention relates to a process for the production of a methane-containing gas and, of special interest in this connection, is the production of a gas having a methane content of at least 80 percent by volume which, on account of its high methane content may, for instance, find an application as an exchange gas for natural gas. In accordance with the invention, such a methane-containing gas may be produced from a gas obtained by the partial oxidation (gasification) of solid and/or liquid fuels such as, for instance, coals and oils. The gas of partial oxidation which is to be transformed may be desulfurized and subjected to a methanization reaction in the presence of a catalyst such as, for example, a nickel-containing catalyst, which is suited for this purpose, that is, the methanization reaction may be carried out catalytically.

According to one advantageous feature of the process of the invention, the desulfurized gas of partial oxidation is admitted into a methanizing reactor with a water vapor addition and without previously subjecting the gas to a conversion reaction. In other words, the process according to the invention makes it unnecessary to subject the gas to a conversion reaction prior to the methane-forming reaction. Favorably, a gas-liquid contacting device is arranged both upstream and downstream of the methanizing reactor with the two gas-liquid contacting devices being in communication with one another via a common water flow circuit from which water vapor added to the gas prior to the methanization may be withdrawn in whole or in part.

The invention thus makes it possible to completely forego a conversion of the gas of partial oxidation prior to the methanization. However, it is preferable in any event for a quantity of water vapor within definite limits to be added to the gas before the latter enters the methanizing reactor since the water vapor may serve to reduce or minimize the deposition of carbon from the gas during the methanization reaction, which deposition might occur due to the presence of a carbonaceous component such as carbon monoxide in the gas. By virtue of the advance provided by the invention according to which this water vapor may, at least predominately, be withdrawn from the water flow circuit of the gas-liquid contacting devices which span the methanizing reactor, this water vapor addition need not, however, constitute a source of great expense. The savings on apparatus and operating costs which it is possible to obtain by elimination of the conversion reaction prior to the methanization reaction may, therefore, be practically completely realized as profits.

The methanization reaction is advantageously carried out under isothermal conditions and, preferably, at temperatures between about 330 and 450°C and under pressures in the range of about 3 to 60 atmospheres in excess of atmospheric pressure. The water vapor addition to the gas of partial oxidation is favorably so regulated that, upon entry into the methanizing reactor, there exists a relationship between gas and water vapor, that is, a ratio of water vapor to gas, such that about 0.6 to 1.6 kilograms of water vapor per normal cubic meter of gas is present. Of course, the particular ratio of water vapor to gas which is most advantageously used in a given instance is dependent upon the origin of the gas of partial oxidation. For instance, in the case of a gas of partial oxidation which is obtained by the gasification of coal, the ratio of water vapor to gas is advantageously of the order of 1.2 kilograms of water vapor per normal cubic meter of gas whereas, in the case of a gas of partial oxidation obtained by the gasification of fuel oil, this ratio is advantageously of the order of 0.85 kilograms of water vapor per normal cubic meter of gas.

The invention further provides an arrangement for the production of methane-containing gases, particularly gases containing at least 80 percent by volume of methane, which includes means defining a flow path for a gaseous substance and means in at least one portion of the flow path for subjecting the gaseous substance to a methanization reaction in the presence of a predetermined amount of water vapor. In another portion of the flow path downstream of the aforesaid one portion, there is provided means for cooling the gaseous substance with cooling water. The novel arrangement also comprises means for admitting the cooling water, subsequent to the cooling operation, into a region of the flow path such that a quantity of the cooling water is present in the aforesaid one portion of the flow path in vapor form during the reaction and at least partially constitutes the predetermined amount of water vapor. Means is further provided for conveying residual cooling water from the aforesaid region of the flow path to the aforesaid other portion of the flow path for use in the cooling operation.

The arrangement including the features just outlined is well-suited for carrying out the process according to the invention. For performing the process of the invention, a so-called isothermal reactor is particularly suitable for use as a methanizing reactor. Where such an isothermal reactor is used, it is favorable for the conduit system of the reactor, which system may function as a heat-exchanger, to be in communication with a vapor or steam generating device. Naturally, it is also possible to use other suitable types of reactors which permit isothermal operation.

The gas-liquid contacting devices may, with advantage, be constructed as so-called packed column saturators. However, here also, the use of other constructions is not out of the question and may be utilized.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

The single FIGURE is a somewhat diagrammatic representation of one form of an arrangement in accordance with the invention which may be used for carrying out the process of the invention.

DESCRIPTION OF THE PREFERRED EMBODIMENTS

For the purpose of gaining a better understanding of the invention, the process of the invention will be further illustrated with reference to the FIGURE using two examples of different gases which are to be treated so as to produce a methane-containing gas. Example 1 relates to the treatment of a crude gas which has been obtained by the partial oxidation of coal. In contrast, Example 2 relates to the treatment of a crude gas which has been obtained by the partial oxidation of fuel oil. These crude gases have the following compositions in terms of percent by volume:

|  | Example 1 (starting material: coal) | Example 2 (starting material: fuel oil) |
|---|---|---|
| $CO_2$ + sulfur compounds | 10.0 | 5.0 |
| CO | 58.5 | 47.0 |
| $H_2$ | 30.4 | 47.0 |
| $CH_4$ | 0.1 | 0.1 |
| $N_2$ | 1.0 | 0.9 |
|  | 100.0 | 100.0 |

The crude gas is first conveyed into a desulfurizing device 17. Here, it is purified from the sulfur compounds contained in the gas to such an extent that the residual sulfur content of the gas is suitable for the subsequent catalytic treatment. In the present case, the gas is assumed to be purified to such an extent that the residual total sulfur in the gas amounts to less than 1 part per million. The removal of sulfur from the gas is performed in conventional manner.

After the desulfurization, the gas flows through a conduit 1 and, from there, into a lower end of a gas-liquid contacting device 2 which, in the present instance, is assumed to be constructed as a packed column saturator. Highly heated water from a water flow circuit is admitted into the saturator 2 at an upper end thereof, this water being conveyed to the saturator 2 via a conduit 12. As a result, there occurs in the saturator 2 a substantial saturation of the gas with water vapor. As will be appreciated, the gas flows through the saturator 2 countercurrent to the circuit water.

The at least partially saturated gas next leaves the saturator 2 and flows into a conduit 13. In those cases where it may be necessary, additional water vapor may be introduced into the stream of gas subsequent to its leaving the saturator 2 via a conduit 3 provided for this purpose and which opens into the conduit 13. In any event, the gas is conveyed through the conduit 13 towards a methanizing reactor 5.

Prior to entering the reactor 5, the gas passes through a heat exchanger 4. Here, the gas stream is preheated by heat exchange with gas which has already been methanized and is leaving the reactor 5. The gas stream entering the reactor 5 is heated to the temperature required to initiate the catalytic methanization reaction, namely, about 270° to 300°C in the present case.

In the reactor 5, the heated gas stream is transformed, that is, undergoes a methanization reaction, at the required reaction temperature. In the case being presently discussed, the reactor 5 is assumed to be filled with a conventional nickel-containing methanization catalyst. Not only does the methanization of carbon monoxide and carbon dioxide according to the equations (2) and (3) above occur in the presence of this catalyst but, simultaneously, a reaction of excess carbon monoxide with water vapor also occurs in accordance with the following relationship:

$$CO + H_2O \quad CO_2 + H_2 \tag{4}$$

In the embodiment illustrated, the reactor 5 is constructed as a so-called isothermal reactor and is provided with a conduit system 14 which serves as heat exchange means. The conduit system 14 communicates with a vapor or steam generating device 6. By means of the hot water or other suitable heat exchange fluid circulating in the conduit system 14, it is possible to maintain the temperature along the entire length of the catalyst bed in the reactor 5 substantially constant. The heat absorbed by the circulating water, which corresponds to heat generated by the exothermic methanization reaction, may be used in the steam generating device 6 for the production of high pressure steam. The high pressure steam produced may be withdrawn from the steam generating device 6 via a conduit 7 provided for this purpose. This high pressure steam may be used for the operation of steam turbines or, on the other hand, may also be used as additional water vapor for introduction into the gas stream through the conduit 3.

After leaving the reactor 5, the transformed gas now enters the heat exchanger 4 in which it undergoes a first cooling stage while preheating the gas stream flowing towards the reactor 5. Subsequently, the transformed gas flows through a conduit 15 and is admitted from there into a lower end of a gas-liquid contacting device 8 which, in the present case, is likewise constructed as a packed column saturator. Cooled water from the water flow circuit is admitted into the saturator 8 at an upper end thereof. This water corresponds to excess water which has flowed off from the saturator 2 and has been conveyed to the saturator 8 by means of a cold water pump 11 via a conduit 16, the excess water having been cooled by its contact with the gas in the saturator 2. As a result of being sprayed by the cooled water, the hot gas in the saturator 8 is further cooled. The water vapor accompanying the gas is condensed here and, simultaneously, the circuit water is heated to a high temperature by virtue of its contact with the hot gas. After flowing off from the saturator 8, the water which has been used for the cooling may, together with the water which has condensed from the gas, again be pumped back to the saturator 2 via the conduit 12 with the aid of a hot water pump 10. Thus, the water flow circuit between the two saturators 2 and 8 is closed.

The cooled gas may be withdrawn from the saturator 8 via a conduit 9. The gas entering the conduit 9 has the following composition in terms of volume percent:

|  | Example 1 (starting material: coal) | Example 2 (starting material: fuel oil) |
|---|---|---|
| $CO_2$ | 65.1 | 52.7 |
| CO | 0.1 | 0.1 |
| $H_2$ | 3.1 | 3.6 |
| $CH_4$ | 30.3 | 42.0 |
| $N_2$ | 1.4 | 1.6 |
|  | 100.0 | 100.0 |

In both cases, the methanization reaction was carried out at a pressure of 25 atmospheres in excess of atmospheric pressure and at a temperature of 350°C. For Example 1 (starting material: coal), the ratio of water vapor to gas was 1.15 kilograms of water vapor per normal cubic meter of gas whereas, for Example 2 (starting material: fuel oil), this ratio was 0.82 kilograms of water vapor per normal cubic meter of gas.

The gases withdrawn from the saturator 8 through the conduit 9 may next be freed of carbon dioxide in conventional manner by passing them through a carbon dioxide scrubbing device 18. Thereafter, methane-containing gases having the following compositions, in terms of volume percent, are obtained:

|  | Example 1 (starting material: coal) | Example 2 (starting material: fuel oil) |
|---|---|---|
| CO | 0.2 | 0.1 |
| $H_2$ | 8.7 | 7.6 |
| $CH_4$ | 87.1 | 88.8 |
| $N_2$ | 4.0 | 3.5 |
|  | 100.0 | 100.0 |

These gases may, without further ado, be used as exchange gases for natural gas. However, it is also possible to subject the gases to an after-treatment in conventional manner both before and after removal of carbon dioxide therefrom.

Although this has not been illustrated for the sake of clarity, it will be appreciated that suitable conveying means may be provided for the gas to be treated.

It will be understood that each of the elements described above, or two or more together, may also find a useful application in other types of processes and arrangements differing from the type described above.

While the invention has been illustrated and described as embodied in a process and arrangement for the production of methane-containing gases, it is not intended to be limited to the details shown since various modifications and structural changes may be made without departing in any way from the spirit of the present invention.

Without further analysis, the foregoing will so fully reveal the gist of the present invention that others can by applying current knowledge readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A continuous process for methanizing the gaseous product obtained in the partial oxidation of coal or heavy hydrocarbon oil comprising the steps, carried out in continuous operation, of
   a. passing said gaseous oxidation product, as obtained from said oxidation process and without preceding modification of its carbon monoxide, carbon dioxide or hydrogen contents, in countercurrent through high temperature water in a gas-liquid contact tower so as to at least partially saturate the gas with water vapor;
   b. then passing the gas from said saturation tower into a catalytic reactor and there bringing it in contact with a nickel catalyst at a temperature of about 330° to 450°C and a pressure of about 3 to 60 atm above atmospheric so as to methanize the gas;
   c. then passing the gas into a second gas-liquid contact tower and moving it in countercurrent to cooling water so as to cool it and dry it by condensation of the accompanying water vapor, and
   d. withdrawing and recovering the gas having a high methane content from said cooling tower;
   the said high temperature saturation water and water vapor and the said cooling water being moved in a single closed flow circuit between said two towers, the high temperature water and steam being obtained from the heat exchange between the cooling water and the hot methanized gas in said cooling tower and being passed through a portion of said flow circuit from the bottom of said cooling tower to the head of said saturation tower,
   and the said cooling water being obtained from the heat exchange between the high temperature water and the fresh incoming gas and being passed through another portion of said flow circuit from the bottom of said saturation tower to the head of said cooling tower.

2. The process of claim 1 wherein the said gaseous oxidation product is subjected to desulfurization prior to entering said saturation tower.

3. The process of claim 1 wherein the high methane content gas after removal from the cooling tower is subjected to removal of the carbon dioxide contained therein.

4. The process of claim 1 wherein the saturated gas is further preheated prior to entering the reactor to a temperature of about 270° to 300°C with the hot methanized gas flowing from the reactor to the cooling tower.

5. The process of claim 1 wherein the circulation of the water in the closed circuit is power-forced.

6. The process of claim 1, wherein steam is added to the gas from an external source to increase the saturation of the gas with water vapor.

7. The process of claim 6 wherein the steam is added to the flow of saturated gas from said saturation tower prior to entering of the gas into the reactor.

8. The process of claim 1 wherein the temperature in the reactor is maintained substantially constant by a heat exchange system while the excess steam generated in the system is withdrawn for external use.

9. An apparatus for methanizing the gaseous product obtained in the partial oxidation of coal or heavy hydrocarbon oil, the said apparatus comprising a saturation tower for at least partially saturating the gas with water vapor, an inlet for the gaseous oxidation product disposed at the lower portion of said saturation tower, a reactor vessel for bringing the gas in contact with the catalyst in order to methanize it, a cooling tower for cooling the hot methanized gas, an outlet at the upper portion of said cooling tower for discharging the methanized gas, gas conduit means for passing the at least partially saturated gas from the top portion of the reactor vessel and for passing the methanized gas from the bottom portion of the reactor vessel to the lower portion of the cooling tower, water conduit means for passing high temperature water from the bottom of the cooling tower to the head of the saturation tower and passing cooling water from the bottom of the saturation tower to the head of the cooling tower and means for withdrawing the cooled methanized gas from the apparatus, the said means for passing heated water and means for passing cooling water, together with said two towers, forming a closed flow circuit.

10. The apparatus of claim 9 which includes separate pumps disposed in said flow circuit for moving the high temperature water and the cooling water.

11. The apparatus of claim 9 which includes means for admitting steam to said gas from an external source at a point prior to where said gas conduit means leads into said reactor.

12. The apparatus of claim 9 which includes heat-exchange means disposed ahead of the reactor vessel and adapted to provide heat-exchange between the at least partially saturated gas and the methanized gas whereby a preheating of the circulating gas is effected prior to the methanized reaction.

* * * * *